United States Patent [19]

Schobel

[11] Patent Number: 4,687,662

[45] Date of Patent: Aug. 18, 1987

[54] THERAPEUTIC EFFERVESCENT COMPOSITION

[75] Inventor: Alexander M. Schobel, North Plainfield, N.J.

[73] Assignee: Warner-Lambert Company, Morris Plains, N.J.

[21] Appl. No.: 819,093

[22] Filed: Jan. 15, 1986

Related U.S. Application Data

[63] Continuation-in-part of Ser. No. 775,931, Aug. 30, 1985, abandoned, which is a continuation-in-part of Ser. No. 740,144, May 31, 1985, abandoned.

[51] Int. Cl.[4] .................... A61K 31/60; A61K 37/00; A61K 31/13; A61L 9/04

[52] U.S. Cl. .................................... 424/44; 514/159; 514/557; 514/579; 514/960

[58] Field of Search ................. 424/44; 514/557, 579, 514/159, 960

[56] References Cited

U.S. PATENT DOCUMENTS

| | | | |
|---|---|---|---|
| 3,325,357 | 6/1967 | Irani | 424/44 |
| 3,773,922 | 11/1973 | Gergely | 424/44 |
| 3,882,228 | 5/1975 | Boncey et al. | 424/44 |
| 4,093,710 | 1/1973 | Sass et al. | 424/44 |
| 4,309,408 | 1/1982 | Pathak et al. | 424/44 |

FOREIGN PATENT DOCUMENTS

| | | | |
|---|---|---|---|
| 1328591 | 8/1973 | United Kingdom | 424/44 |

OTHER PUBLICATIONS

Chem. Abst. 183: 166166d, 1985.

*Primary Examiner*—Johnnie R. Brown
*Assistant Examiner*—John W. Rollins
*Attorney, Agent, or Firm*—Charles A. Gaglia, Jr.; Gary M. Nath

[57] ABSTRACT

Effervescent compositions in the form of tablets or powders comprising a therapeutic agent, a granulating agent, a microparticulate effervescent component and an effervescent system which dissolve rapidly in water to yield an effervescent solution containing a completely dissolved therapeutic agent and a process for their preparation.

14 Claims, No Drawings

THERAPEUTIC EFFERVESCENT COMPOSITION

BACKGROUND OF THE INVENTION

This application is a continuation-in-part of U.S. Ser. No. 775,931 filed Aug. 30, 1985, now abandoned, which is a continuation-in-part of U.S. Ser. No. 740,144 filed May 31, 1985, now abandoned.

FIELD OF THE INVENTION

This invention relates to effervescent compositions in the form of tablets or granules which dissolve rapidly in water to yield an effervescent solution containing a completely dissolved therapeutic agent. The invention also relates to the method by which the therapeutic effervescent compositions may be prepared.

More particularly, the invention relates to a novel, analgesic containing effervescent tablet which completely dissolves in cold water in about 1 minute without stirring to yield a palatable effervescent solution of analgesic.

DESCRIPTION OF THE PRIOR ART

The use of effervescent compositions as a means of administering solubilized therapeutic agents is well known. Dosage forms containing solubilized therapeutic agents have the advantage of being faster acting because they are ready for absorption. When an undissolved therapeutic agent is ingested, it must be dispersed and then solubilized before absorption can take place. All references to drug or therapeutic agent solubility herein refer to solubility in aqueous media.

Effervescent compositions for soluble therapeutic agents are prepared containing the drug to be administered admixed with an effervescent system. Such systems usually comprise an acidifying agent and a carbonate containing compound. When introduced to water, the carbonate containing compound reacts with the acidifying agent to produce a rapid evolution of carbon dioxide gas. This rapid evolution of gas stirs the solution dispersing the therapeutic agent. The stirring is intended to solubilize the therapeutic agent.

Merely placing a therapeutic agent in an effervescent composition does not, however, assure solubilization. The therapeutic agent may be only slightly water soluble and/or may not be wetted by the effervescing solution. A slightly water soluble compound is soluble in from 100 to 1000 parts of solvent per 1 part compound. Achieving complete solubilization of a therapeutic agent is essential to achieving rapid therapeutic relief and avoiding the unpleasant mouthfeel associated with ingesting powder-like suspensions of medicinals. Much effort has been directed toward solubilizing therapeutic agents using effervescent formulations.

U.S. Pat. No. 3,882,228 to Boncey, et al., discloses preparing wettable aspirin particles. The aspirin particles are coated in a spray drying process with a mixture of a water soluble coating material, a wetting agent and/or a water soluble film forming agent. The coated aspirin particles are then incorporated into effervescent tablets.

British Pat. No. 1,328,591 to Bru discloses a soluble acetaminophen effervescent composition. To achieve solubilization of the acetaminophen, Bru mixes the acetaminophen and the carbonate part of the effervescent carbonate and acid couple into a paste with the aid of an appropriate solvent, such as ethanol, then dries and powders the paste. The acid part of the effervescent couple is then mixed with the powdered paste. Vitamin C is then blended with the dried acetaminophen, carbonate and acid containing particles. The resultant blend is then formed into effervescent tablets.

Effervescent products prepared by these techniques are expensive and difficult to process.

SUMMARY OF THE INVENTION

It has unexpectedly been discovered that an effervescent composition can be prepared which may contain up to 30% by weight of a therapeutic agent which when placed in cold water will completely dissolve in less than 1 minute leaving a clear effervescent solution.

DETAILED DESCRIPTION

In particular, it has been found that a therapeutic effervescent composition which dissolves rapidly in cold water to form a clear solution is produced from an admixture of (1) a preblended mixture of
  (A) a granulated therapeutic agent having a particle size of about 100 to about 600 microns, and
  (B) a component of an effervescent system having a particle size of about 50 to about 600 microns, and
(2) an effervescent system.

While the invention is not limited to theoretical considerations, it is believed that rapid and complete solubilization of the therapeutic agent is achieved through the interaction of several factors.

It is believed that the component of the effervescent system having a particle size of about 50 to about 600 microns because of its controlled particle size forms a uniform mixture with the granulated therapeutic agent which has about the same particle size. It is further believed that these particulate materials adhere to each other after mixing with the remaining components of the effervescent composition and that this property results in the formation of an extremely uniform effervescent composition which rapidly disintegrates in cold water dispersing the granulated therapeutic agent. It is believed that granulating prevents segregation of the therapeutic agent during mixing to form the effervescent composition and prevents agglomeration in solution after its release from the composition.

The particles of therapeutic agent are of a specific bulk density to optimize the rate of solubilization. Particles of very low bulk density do not wet well when released from an effervescent composition and form a floating film on the solution surface. Particles of a high bulk density fall to the bottom of the solution and dissolve slowly, apparently due to decrease stirring at the bottom of the solution and decreased surface area of the particles.

It is believed that all of the above factors work together to form a rapid dissolving effervescent composition of a therapeutic agent.

Accordingly, a rapid dissolving, effervescent composition containing a therapeutic agent which forms a clear solution in cold water comprises: a preblended mixture present in an amount from about 7 to about 57.5% by weight of (A) a granulated therapeutic agent having a particle size of about 100 to about 600 microns of
  (1) a therapeutic agent in an amount from about 2 to about 27% by weight, and (2) a granulating agent present in an amount from about 0.03 to about 2.5% by weight, and (B) a component of an effervescent system having a particle size from about 50 to about 600 microns in an amount from about 5 to about 30% by weight, and an effervescent system in an amount from about 42.5 to about 90% by weight has been discovered.

In the instant invention, the therapeutic agent can be any soluble or slightly soluble therapeutic agent or nutrient suitable for oral administration in an aqueous solution.

Suitable thereapeutic agents that may be employed in the instant composition may vary widely and generally represent any stable therapeutic agent and combination of therapeutic agents. Illustrative categories and specific examples include:

(a) Antitussives, such as dextromethorphan, dextromethorphan hydrobromide, noscapine, carbetapentane citrate, and chlophedianol hydrochloride;
(b) Antihistamines, such as chlorpheniramine maleate, phenindamine tartrate, pyrilamine maleate, doxylamine succinate, and phenyltoloxamine citrate;
(c) Decongestants, such as phenylephrine hyrdochloride, phenylpropanolamine hydrochloride, pseudoephedrine hydrochloride, ephedrine;
(d) Various alkaloids, such as codeine phosphate, codeine sulfate and morphine;
(e) Mineral supplements such as potassium chloride and calcium carbonates, magnesium oxide and other alkali metal and alkaline earth metal salts;
(f) Laxatives, vitamins and antacids;
(g) Ion exchange resins such as cholestyramine;
(h) Anti-cholesterolemic and anti-lipid agents;
(j) Antipyretics and analgesics such as acetaminophen, aspirin and ibuprofen;
(k) Appetite suppressants such as phenylpropanolamine hydrochloride or caffeine;
(l) Expectorants such as guaifenesin;
(m) Anti-inflammatory agents such as isoxicam, and meclophenamic acid; and
(n) Antibiotics such as neomycin, tetracycline, and the polymixins.

Additional useful therapeutic agents include coronary dilators, cerebral dilators, peripheral vasodilators, anti-infectives, psychotropics, antimanics, stimulants, gastro-intestinal sedatives, antidiarrheal preparations, anti-anginal drugs, vasodialators, anti-hypertensive drugs, vasoconstrictors and migrane treatments, tranquilizers, antipsychotics, antitumor drugs, anticoagulants and antithrombotic drugs, hypnotics, sedatives, anti-emetics, anti-nauseants, anticonvulsants, neuromuscular drugs, hyper- and hypoglycaemic agents, thyroid and antithyroid preparations, diuretics, antispasmodics, uterine relaxants, mineral and nutritional additives, anti-obesity drugs, anabolic drugs, erythropoietic drugs, antiasthmatics, expectorants, cough suppressants, mucolytics, anti-uricemic drugs, and the like.

Mixtures of the therapeutic agents may also be used.

The therapeutic agent is present in a therapeutically effective amount from about 2 to about 27% by weight of the effervescent composition. In a preferred embodiment, the therapeutic agent is an analgesic selected from the group consisting of acetaminophen, aspirin, ibuprofen, and the like, and mixtures thereof. In a more preferred embodiment, the therapeutic agent is acetaminophen having a bulk density from about 0.2 to about 0.6 g/ml. The usual dose of acetaminophen is about 325 to about 1000 mg every four hours. A bulk density less than about 0.2 g/ml leaves a powdery mass floating on the surface of the effervescent solution. A bulk density greater than about 0.6 g/ml leaves undissolved particles on the bottom of the effervescent solution. In a preferred embodiment, the bulk density is from about 0.25 to 0.5 g/ml. In a more preferred embodiment, the bulk density is from about 0.35 to 0.47 g/ml. In a preferred embodiment, the therapeutic agent is present from about 9 to 25% by weight. In a more preferred embodiment, the therapeutic agent is present from about 12% to about 20% by weight.

The granulating agent used in this invention can be any water soluble pharmaceutically acceptable granulating agent having a viscosity below 100 cps, 10% by weight, at 25° in water, and being compatable with the therapeutic agent. The granulating agent may be selected from the group consisting of water, alcohol, polyvinylpyrrolidone, sucrose, hydroxypropyl cellulose and mixtures thereof. The preferred granulating agent for use in the instant invention is polyvinylpyrrolidone.

The granulating agent is present in the instant invention in an amount from about 0.03 to about 2.5% by weight. Less than about 0.03% granulating agent causes a residue of surface film containing undissolved therapeutic agent to form. Greater than about 2.5% causes slow disintegration. In a preferred embodiment, the granulating agent is present in an amount from about 0.05 to about 2.0% and more preferably in an amount from about 0.08 to about 0.23%.

The granulating formed by combining the therapeutic agent with granulating agent is ground and screened such that it has a particle size from about 100 to about 600 microns. A particle size of less than 100 microns yields a chalky material which results in processing problems such as poor mixing and compressibility properties. A particle size of greater than 600 microns causes a slow rate of solubilization and will leave undissolved therapeutic agent on the bottom of the effervescent solution after disintegration of the effervescent composition. In a preferred embodiment, the granulation has a particle size of about 100 to about 400 microns and more preferably has a particle size of about 125 to about 225 microns. In a preferred embodiment, the granulation has a particle size from about 125 to about 175 microns and acetaminophen is the therapeutic agent.

The effervescent system may comprise one or more components. The component of the effervescent system blended with the granulated therapeutic agent is in a microparticulate form having a particle size from about 50 to about 600 microns. In a preferred embodiment, the effervescent system comprises a carbonate containing material and an acid. The microparticulate component of the effervescent system may be the carbonate containing material, the acid and mixtures thereof.

In a preferred embodiment, the microparticulate component of the effervescent system is the acid. The microparticulate acid has a particle size of from about 50 to about 600 microns. A particle size of less than 50 microns promotes excessive static charge and results in processing problems such that the acid will not mix uniformly with the granulation and the mixture will not flow consistently. A particle size of greater than 600 microns causes slow disintegration. In a preferred embodiment, the microparticulate acid has a particle size of about 50 to about 275 microns and more preferrably has a particle size of about 75 to about 175 microns. The microparticulate acid is present in an amount from about 5 to about 30% such that the total acid content of the effervescent composition is from about 22 to 46% by weight. Microparticulate acid content of less than about 5% results in slow disintegration and slow rate of solution of the therapeutic agent. Microparticulate acid content greater than about 30% results in processing difficulties such as poor flow, and mixing as well as capping during tablet manufacture. In a preferred embodiment, the microparticulate acid is present in the amount of about 7.5 to about 22.5% by weight. In a more preferred embodiment, the microparticulate acid is present in the amount of about 10 to about 17%.

The acids which may be employed in practicing the present invention are compounds capable of reacting with carbonate containing materials to cause the release of carbon dioxide when contacted with sufficient water. Suitable acids include citric acid, fumaric acid, adipic acid, malic acid, tartaric acid, and the like, including mixtures thereof. The preferred acid is citric acid. In a preferred embodiment, the non-microparticulate acid has a particle size greater than 600 microns. This larger particle size is necessary to prevent manufacturing problems such as capping.

In the instant invention, the same acid is usually employed in the preblended mixture component and in the effervescent system, however, it is within the scope of the present invention for the two components to contain different acids including different mixtures of acids.

The granulated therapeutic agent and microparticulate acid are admixed to form the preblended mixture. The preblended mixture is present in the instant invention in an amount from about 7 to about 57.5% by weight. In a preferred embodiment the preblended mixture component is present from about 20 to about 35% by weight and more preferably is present from about 25 to about 30% by weight.

The effervescent system comprises all the ingredients of the rapid dissolving, effervescent composition except those contained in the preblended mixture. The effervescent system is present in an amount from about 42.5 to about 90% by weight.

The effervescent system may be selected from a wide variety of materials that are capable of producing effervescence in water. A particularly preferred method uses carbonate containing materials.

The carbonate containing materials which may be employed in practicing the present invention are compounds which are capable of reacting with acidic compounds with the release of carbon dioxide when contacted with sufficient water. In particular, the inorganic carbonates, and more particularly the alkali metal and ammonium carbonate materials may be used. Illustrative compounds include sodium carbonate, sodium bicarbonate, sodium sesquicarbonate, potassium carbonate, potassium bicarbonate, lithium carbonate, lithium bicarbonate, ammonium carbonate, ammonium bicarbonate, ammonium sesquicarbonate and the like, including mixtures of these.

The carbonate containing materials, when used, are present in an amount from about 40 to about 60% by weight of the total therapeutic effervescent composition.

The therapeutic effervescent composition may additionally contain conventional additives such as lubricants, antifoaming agents, flavoring agents, colorants, sweeteners and glidants.

The lubricant used in the present invention can be any pharmaceutically acceptable lubricant which includes metallic stearates, stearic acid, hydrogenated vegetable oils, polyethylene glycols, corn starch, sodium benzoate, sodium acetate and the like or mixtures thereof. Sodium benzoate is the preferred lubricant of the present invention. The lubricant is present in an amount from about 1.7 to about 10% by weight.

The antifoaming agent used in the present invention can be any pharmaceutically acceptable antifoaming agent which includes simethicone and the like, or mixtures thereof. Simethicone is the preferred antifoaming agent of the present invention. The antifoaming agent is present in an amount from about 0.05 to about 0.22% by weight.

Suitable flavoring agents include both natural and artificial flavors, and mints such as peppermint, menthol, artificial vanilla, cinnamon, various fruit flavors, both individual and mixed, and the like are contemplated. The flavorings are generally utilized in amounts that will vary depending upon the individual flavor, and may, for example, range in amounts of about 0.5 to about 3% by weight of the final composition weight.

In the instance where sweeteners are utilized, the present invention contemplates the inclusion of those sweeteners well known in the art, including both natural and artificial sweeteners. Thus, additional sweeteners may be chosen from the following non-limiting list: sugars such as sucrose, glucose (corn syrup), invert sugar, fructose, and mixtures thereof; saccharin and its various salts such as the sodium or calcium salt; cyclamic acid and its various salts such as the sodium salt; the dipeptide sweeteners such as aspartame; dihydrochalcone; glycyrrhizin; *Stevia rebaudiana* (Stevioside); and sugar alcohols such as sorbitol, sorbitol syrup, mannitol, xylitol, and the like. Also contemplated as an additional sweetener is the nonfermentable sugar substitute (hydrogenated starch hydrolysate) which is described in U.S. Pat. No. Re 26,959. Also contemplated is the synthetic sweetener 3,6-dihydro-6-methyl-1-1-2,3-oxathiazin-4-one-2,2-dioxide particularly the potassium (Acesulfame-K), sodium and calcium salts thereof as described in German Pat. No. 2,001,017.7. The sweeteners are used in amounts of up to about 5% by weight. In general, the amount of sweetener will vary according to the type of sweetener and the desired taste of the final product. Natural sweeteners are generally used in amounts up to about 5% by weight. In contrast, artificial sweeteners are used in amounts up to about 1% by weight.

The colorants useful in the present invention include the pigments, such as titanium dioxide, that may be incorporated in amounts of up to about 1% by weight, and preferably up to about 0.6% by weight. Also, the colorants may include other dyes suitable for food, drug and cosmetic applications, and known as F.D. & C. dyes and the like. The materials acceptable for the foregoing spectrum of use are preferably water-soluble. Illustrative examples include indigoid dye, known as F.D. & C. Blue No. 2, which is the disodium salt of 5,5'-indigotin disulfonic acid. Similarly, the dye known as F.D. & C. Green No. 1, comprises a triphenylmethane dye and is the monosodium salt of 4-[4-N ethyl-p-sulfobenzylamino)diphenylmethylene][1-(N-ethyl-N-p-sulfoniumbenzyl)-2,5-cyclohexadienimine]. A full recitation of all F.D. & C. and D. & C. dyes and their corresponding chemical structures may be found in the Kirk-Othmer Encyclopedia of Chemical Technology, in Volume 5, at Pages 857-884, which text is accordingly incorporated herein by reference.

In the instance where glidants are utilized, the present invention contemplates glidants such as microfine silicas, corn starch, microcrystalline cellulose, metallic stearates and the like, including mixtures of these that may be incorporated in amounts up to about 2%.

A process for preparing the rapid dissolving therapeutic effervescent composition has also been unexpectedly discovered. The process comprises:

(A) forming a granulation by dissolving a granulating agent in a solvent to form a solution and mixing the solution into the therapeutic agent;

(B) drying the granulation;

(C) sizing the dried granulation;

(D) admixing a microparticulate component of an effervescent system with the sized granulation of step (C) to form a mixture, and (E) mixing an effervescent system with the mixture of step (D) to obtain a uniform mixture of granules and recovering the product.

More specifically, the process involves dissolving the granulating agent in an amount from about 0.03 to about 2.5% by weight in a solvent to form a solution containing from about 1 to about 50% by weight granulating agent, mixing the therapeutic agent with the solution of granulating agent and solvent to form a granulation, drying the granulation at between about 50 to about 70° C., sizing the dried granulation by grinding and screening to obtain particles having a size of about 100 to about 600 microns, admixing the microparticulate acid with the sized granulation; mixing the antifoaming agent, the carbonate containing material, the acid, the lubricant, the sweetener, and flavors to form a uniform effervescent system containing mixture; blending this effervescent system containing mixture with the granulation and microparticulate acid mixture and recovering the product. The final product may be used as is or formed into any desirable shape such as a tablet to render the product suitable for providing the necessary amount of therapeutic agent.

The present invention is further illustrated by the following examples. All parts and percentages in the examples and throughout the specification and claims are by weight of the total effervescent composition.

EXAMPLE I

Inventive Run 1

This example demonstrates the formation of a product of this invention.

The following ingredients were admixed in accordance with the procedure listed below.

| Ingredient | Percent by Weight in the Final Product |
|---|---|
| Therapeutically Active Component | |
| Acetaminophen | 14.05 |
| Polyvinylpyrrolidone | 0.17 |
| Distilled Water (80 ml) | — |
| Citric Acid, microparticulate | 14.05 |
| Effervescent Component | |
| Sodium Bicarbonate | 47.77 |
| Simethicone | 0.14 |
| Distilled Water (5 ml) | — |
| Citric Acid | 14.05 |
| Sodium Carbonate | 4.78 |
| Sugar | 1.69 |

-continued

| Ingredient | Percent by Weight in the Final Product |
|---|---|
| Sodium Benzoate | 3.30 |

Dissolve the polyvinylpyrrolidone in distilled water (80 ml). Slowly add the polyvinylpyrrolidone solution to the acetaminophen while mixing. Dry the resultant granulation at 60° C. until dried. Size the dried granulation through an oscillating granulator equipped with a No. 60 mesh screen (U.S. standard). Microparticulate citric acid (50 to 600 microns) was blended with the sized granulation.

Disperse the simethicone in 100 g of sodium bicarbonate.

Add distilled water (5 ml) to the remainder of the sodium bicarbonate while mixing, then add with continued mixing the citric acid, sodium carbonate, the active granulation-citric acid blend, the sugar, the simethicone-sodium bicarbonate blend, and sodium benzoate and mix until a uniform blend is obtained. Compress tablets using flat faced beveled edged tooling to a weight of 3.56 g having a diameter of 15/16 inches and a hardness of 7-9 strong cobb hardness units.

Tablets made by the inventive procedure and the inventive formula described above disintegrated rapidly in 55 seconds with no undissolved drug residue when placed in 200 ml of water at 22° C.

EXAMPLE II

Inventive Run B and Comparative Runs A & C

This Example demonstrates the effect bulk density of the therapeutic agent has on the dissolution of a product prepared by the process and composition of Example I. The same amount of acetaminophen as used in Example I was used in each product given below. The bulk density of the acetaminophen varies.

| | FORMULATION | | |
|---|---|---|---|
| Property | Comparative A | Inventive B | Comparative C |
| Bulk Density of Acetaminophen | 0.144 to 0.176 g/ml | 0.353 to 0.465 g/ml | 0.674 to 0.802 g/ml |
| Disintegration | 50 sec. | 55 sec. | 55 sec. |
| pH | 6.15 | 6.15 | 6.15 |
| Appearance | Clear solution powder on liquid surface | No powder on surface, clear solution, no undissolved drug | Clear solution, slight undissolved drug on bottom |
| Residue after 5 minutes | Slight residue on surface | Clear, no undissolved drug | Clear solution, slight residue of drug on bottom |

The results indicate that the product made by inventive formulation B with acetaminophen having a bulk density between 0.353 to 0.465 g/ml is the only product without undissolved drug after disintegration of the tablet and 5 minutes after the tablet was placed in water.

Product A was made with acetaminophen having a bulk density less than 0.2 g/ml. This resulted in undissolved drug floating on the surface of the solution.

Product C was made with acetaminophen having a bulk density greater than 0.6 g/ml. This results in undissolved drug on the bottom of the solution.

The disintegration test is conducted by placing 1 tablet into 200 ml of water at 22° C. Observations are made at the time of complete disintegration of the tablet and at 5 minutes after the start of the test.

EXAMPLE III

Inventive Run 1 and Comparative Products D,E,F,G & H

This Example demonstrates comparative results between the inventive composition and 5 similar commercial products after disintegration in 200 ml of water at 22° C.

| Product | Disintegration Time | pH | Post Disintegration Appearance Initial | 5 Minutes |
|---|---|---|---|---|
| Inv. | | | | |
| 1 | 55 sec. | 6.15 | Clear, no undissolved drug | Clear, no undissolved drug |
| Comp. | | | | |
| D | 5 min. | 5.90 | Surface film cloudy solution | Surface film, undissolved tablet sediment and drug |
| E | 75 sec. | 6.10 | Surface film, undissolved drug | Considerable undissolved drug |
| F | 75 sec. | 6.15 | Surface film, undissolved drug | Considerable undissolved drug |
| G | 90 sec. | 5.30 | Frothy, foaming, cloudy liquid | Cloudy liquid, no particulate material |
| H | 120 sec. | 6.05 | Clear solution, undissolved drug on surface | Clear solution, undissolved drug on surface |

The results clearly demonstrate that only the inventive composition 1, prepared by the formulation and procedure of Example I, results in a clear, palatable, effervescent solution at the end of disintegration and at 5 minutes after disintegration. Products D to H inclusive are commercially available products.

The presence of undissolved drug on the surface of the liquid or suspended throughout the liquid after disintegration of the tablet is considered to render the product unpalatable. All six products tested contained 500 mg of acetaminophen as the active ingredient. Disintegration was in 200 ml of water at 22° C.

EXAMPLE IV

Inventive Runs 2, 3 & 4 and Comparative Runs I, J & K

This Example demonstrates the effect of acetaminophen/polyvinylpyrrolidone granulation particle size on the dissolution of a product prepared by the process and composition of Example I. The acetaminophen/polyvinylpyrrolidone granulation of Example I was sized through U.S. standard mesh screens to produce granulation of various particle sizes.

| Product | U.S. Standard Mesh Size | Typical Particle Size | Results of Dissolution Test |
|---|---|---|---|
| Comparative | | | |
| I | 10 | 850 microns | Poor dissolution, undissolved drug present |
| J | 20 | 650 microns | Poor dissolution, undissolved drug present |
| K | 40 | 275 microns | Undissolved drug present |
| Inventive | | | |
| 2 | 60 | 175 microns | No undissolved drug good dissolution |
| 3 | 80 | 125 microns | No undissolved drug, good dissolution |
| 4 | 100 | 100 microns | No undissolved drug, good dissolution |

The results indicate that product made with acetaminophen/polyvinylpyrrolidone having a particle size corresponding to a 40 mesh U.S. standard screen (400 microns) or larger is unacceptable as it forms a product that does not completely dissolve. Granulation having a particle size less than 400 microns forms a product containing no undissolved drug.

Dissolution was carried out by placing 1 tablet into 200 ml of water at 22° C.

EXAMPLE V

Inventive Runs 5 to 19 and Comparative Run L

This example demonstrates the effect of polyvinylpyrrolidone content on the dissolution of a product prepared by the process and composition of Example I.

| Product | Polyvinylpyrrolidone (%) | Results of Dissolution Test |
|---|---|---|
| COMPARATIVE | | |
| L | 0 | Undissolved particles on surface, poor drug dispersement |
| INVENTIVE | | |
| 5 | 0.028 | Acceptable dissolution, no undissolved drug |
| 6 | 0.056 | Good dissolution, no undissolved drug |
| 7 | 00844 | Same |
| 8 | 0.113 | Same |
| 9 | 0.141 | Same |
| 10 | 0.169 | Same |
| 11 | 0.197 | Same |
| 12 | 0.225 | Same |
| 13 | 0.253 | Same |
| 14 | 0.281 | Same |
| 15 | 0.309 | Same |
| 16 | 0.337 | Same |
| 17 | 0.671 | Same |
| 18 | 1.319 | Same |
| 19 | 2.068 | Disintegration time > 1.5 min. No undissolved drug. |

The results indicate that product made without polyvinylpyrrolidone, comparative run L, does not completely solubilize and leaves undissolved particles on the surface of the solution after the dissolution test. The results further indicate that polyvinylpyrrolidone content in excess of 2.068% will cause extended disintegration times greater than 1.5 minutes.

Dissolution was carried out by placing 1 tablet into 200 ml of water at 22° C.

This invention being thus described, it will be obvious that the same may be varied in many ways. Such variations are not to be regarded as a departure from the spirit or scope of the invention and all such modifications are intended to be included within the scope of the claims.

I claim:

1. A rapid dissolving therapeutic effervescent composition which comprises:

(1) a preblended mixture present in an amount from about 7 to about 57.5% by weight of (A) a granulated therapeutic agent having a particle size of about 100 to about 600 microns, wherein the granulated therapeutic agent comprises a therapeutic agent present in an amount from about 2% to about 27% by weight selected from the group consisting of acetaminophen, aspirin, ibuprofen and mixtures thereof, and a water soluble granulating agent present in an amount from about 0.03 to about 2.5% by weight, being compatible with the therapeutic agent and having a viscosity below 100 cps, 10% by weight, at 25° C. in water, and (B) a component of an effervescent system having a particle size of about 50 to about 600 microns, present in an amount from about 5% to about 30% by weight said component being selected from the group consisting of a carbonate, an acid and mixtures thereof, and (2) an effervescent system present in an amount from about 42.5% to about 90% by weight wherein the effervescent system comprises a carbonate containing material and an acid, all percentages are by weight of the total effervescent composition.

2. The composition of claim 1 wherein the granulating agent is selected from the group consisting of water, alcohol, polyvinylpyrrolidone. Sucrose, hydroxypropyl cellulose and mixtures thereof.

3. The composition of claim 1 wherein the analgesic is acetaminophen having a bulk density from about 0.2 to about 0.6 g/ml and the granulated therapeutic agent has a particle size of about 100 to about 400 microns.

4. The composition of claim 1 wherein the carbonate containing material is present in an amount from about 40 to about 60% by weight of the effervescent composition.

5. The composition of claim 1 wherein the carbonate containing material is selected from the group consisting of sodium carbonate, sodium bicarbonate, sodium sesquicarbonate, potassium carbonate, potassium bicarbonate, lithium carbonate, lithium bicarbonate, ammonium carbonate, ammonium bicarbonate, ammonium sesquicarbonate and mixtures thereof.

6. The composition of claim 1 wherein the acid is selected from the group consisting of citric acid, fumaric acid, adipic acid, malic acid, tartaric acid and mixtures thereof.

7. The composition of claim 1 wherein the component of an effervescent system in the preblended mixture is an acid having a particle size from about 50 to 600 microns.

8. The composition of claim 1 wherein the acid having a particle size of about 50 to about 600 microns is present in an amount from about 5 to about 30% by weight of the effervescent composition such that the total acid content of the effervescent composition is about 22 to about 46% by weight.

9. The composition of claim 1 wherein the acid is citric acid.

10. The composition of claim 1 wherein the granulating agent is polyvinylpyrrolidone.

11. A method for preparing a rapidly dissolving effervescent composition of a therapeutic agent which comprises:

(A) forming a granulation by dissolving a granulating agent in a solvent to form a solution containing from about 1 to about 50% by weight granulating agent, and mixing a therapeutic agent with the solution, (B) drying the granulation, (C) sizing the dried granulation by grinding and screening to obtain particles having a size of about 100 to about 600 microns.

(D) admixing a component of an effervescent system having a particle size from about 50 to about 600 microns with the sized granulation of step (C) to form a mixture, (E) mixing an effervescent system with the mixture of step (D) to obtain a uniform mixture of granules and recovering the product, wherein said therapeutic agent is selected from the group consisting of acetaminophen, aspirin, ibuoprofen and mixtures thereof, and said granulating agent being compatible with the therapeutic agent, and is water soluble having a viscosity below 100 cps, 10% by weight, at 25° C. in water.

12. The method for preparing a rapid dissolving, effervescent composition of claim 11 wherein the component of an effervescent system in step (D) is an acid.

13. The method for preparing a rapid dissolving, effervescent composition of claim 12 wherein the therapeutic agent is acetaminophen having a bulk density from about 0.2 to about 0.6 g/ml.

14. The method for preparing a rapid dissolving, palatable effervescent composition of claim 12 further comprising forming the mixture of step (E) into a tablet.

* * * * *